United States Patent [19]

Barbieri et al.

[11] Patent Number: 4,981,953

[45] Date of Patent: Jan. 1, 1991

[54] IMMUNOTOXINS, PROCESS FOR THEIR PREPARATION AND PHARMACEUTICAL COMPOSITIONS IN WHICH THEY ARE PRESENT

[75] Inventors: Luigi Barbieri, Bologna, Italy; Pierre Casellas, Montpellier, France; Fiorenzo Stirpe, Bologna, Italy

[73] Assignee: Sanofi, Paris, France

[21] Appl. No.: 73,263

[22] Filed: Jul. 14, 1987

[30] Foreign Application Priority Data

Jul. 15, 1986 [FR] France ............... 86 10297

[51] Int. Cl.$^5$ ............ C07K 15/00; C07K 15/28; C07K 3/06
[52] U.S. Cl. ............... 530/391; 530/390; 530/389; 530/402; 530/403; 530/404; 530/405; 530/406; 530/370; 424/85.91; 514/885
[58] Field of Search ............ 530/389, 390, 391; 424/85.91; 514/885

[56] References Cited

U.S. PATENT DOCUMENTS 4,744,981 5/1988 Pavanasasivan ............... 530/387

FOREIGN PATENT DOCUMENTS 0074279 3/1983 European Pat. Off. .
0169111 1/1986 European Pat. Off. .
2312259 12/1976 France .

OTHER PUBLICATIONS

Olsnes et al., *Pharmac. Ther.*, vol. 15, 1982, pp. 355–381.
Barbieri et al., *Cancer Survey*, vol. 1 (3), 1982, pp. 490–520.
Xuejun et al., *Nature*, vol. 321, 1986, pp. 477–478.
Yeung et al., *Chem. Abst.*, vol. 107, 1987, #333629a.
Gu et al., *Chem. Abst.*, vol. 102, 1984, #56092y.
Gu et al., *chem. Abst.*, vol. 105, 1986, #40684u.
Gu et al., *Chem. Abst.*, vol. 101, 1983, #2509a.
Wang et al., *Chem. Abst.*, vol. 85, 1976, #88802b.
CA, vol. 96, No. 11, 3-15-82, p. 40, No. 97573c.
CA, vol. 95, No. 4, 7-24-81, p. 328, No. 30276y.

*Primary Examiner*—Garnette D. Draper
*Attorney, Agent, or Firm*—Bacon & Thomas

[57] ABSTRACT

The present invention relates to the immunotoxines which are obtained by the covalent coupling of, on the one hand, trichosanthin or trichokirin, as such or appropriately modified with, on the other hand, an antibody or antibody fragment, used in its natural form or correctly modified, which is capable of selectively recognizing an antigen carried by the target cells to be destroyed.

12 Claims, No Drawings

IMMUNOTOXINS, PROCESS FOR THEIR PREPARATION AND PHARMACEUTICAL COMPOSITIONS IN WHICH THEY ARE PRESENT

The present invention relates to products, belonging to the class of the immunotoxins, which are obtained by the covalent coupling of, on the one hand, trichosanthin or trichokirin, as such or appropriately modified (denoted hereafter by the symbol A), with, on the other hand, an antibody or antibody fragment, used in its natural form or correctly modified (denoted hereafter by the symbol P), which is capable of selectively recognizing an antigen carried by the target cells to be destroyed. The 2 proteins can be coupled either via a disulfide bond or via a thioether bond.

Thus, according to one of its features, the present invention relates to an immunotoxin formed by the coupling of an antibody P with trichosanthin or trichokirin—proteins extracted from the plant *Trichosanthes kirilowii*—having the following statistical formula:

$$P'-W-A' \quad (I)$$

in which P' represents the radical of a protein which is an antibody or antibody fragment, as such or appropriately chemically modified, from which at least one of its own groups has been removed and in which the other functional groups are optionally blocked, A' represents the radical of a protein which is trichosanthin or trichokirin, as such or appropriately chemically modified, from which at least one of its own groups has been removed and in which the other functional groups are optionally blocked, and W represents a divalent covalent structure containing at least one thioether group or one disulfide group in which either one of the sulfur atoms is either selected among the ones of the cysteines of P or A or bonded to the groups belonging to P and/or A by spacing structures carrying a functional group bonded to the said groups belonging to P and/or A.

A thioether bond between two proteins is understood as meaning a bond of the type:

in which Z, Y and E are as defined below.

The present invention relates preferentially to an immunotoxin of the statistical formula:

$$P'-W'-A' \quad (II)$$

in which P' and A' are as defined above and W' represents a covalent structure chosen from:

(a) a group of the formula:

(b) a group of the formula:

(c) a group of the formula:

$$-Z'-Y'-E'-S-S-(E-Y-Z)_n- \text{ or}$$

(d) a group of the formula.

$$-S-S-(E-Y-Z)_n-,$$

in which:

Z and Z', which are identical or different, represent the groups belonging to the proteins A and P, chosen from the oxygen atom originating from the hydroxyl of one of the tyrosine residues, the carbonyl group originating from one of the terminal carboxyls or the free carboxyls of the aspartic and/or glutamic acids of A and P, the group originating from the dialdehyde structure obtained after oxidation of the carbohydrate structure of P or optionally of the protein A with periodic acid, and the —NH— group originating from one of the terminal amines of A and P or from one of the amines in the epsilon position of one of the lysine residues;

Y and Y' represent groups covalently bonded to any one of the groups Z and Z' of the proteins A and P, E and E' represent inert spacing structures; and n represents zero or 1.

The immunotoxins of the present invention are represented in simplified form by the formulae (I) and (II) above, but it is understood that there can be several structures W or W' bonded to the same molecule of P and/or A, and hence several A's bonded to a single P and vice-versa, the number of bridges depending on the coupling process and the number of groups belonging to P and A. Thus, the statistical formulae I and II also represent these products and mixtures thereof, which correspond to the formula $P'(W'-A')_m$, in which m is an integer or fraction less than or greater than 1.

For example, if an immunotoxin is formed by the coupling of trichosanthin or trichokirin with the antibody P (for example the antibody T101) via a divalent covalent structure having a disulfide group in which one sulfur is that belonging to a cysteine of trichosanthin or trichokirin and the other is bonded to the phenolic oxygens of the tyrosines of the antibody P by an oxopropyl group, it will have the statistical formula:

$$P'(O-CO-CH_2-CH_2-S-S-A')_t$$

in which t represents the number of tyrosines in the antibody (for example the antibody T101) which are involved in the coupling.

The resulting immunotoxin corresponds to a product of the formula (II) in which:

P' is as defined above, especially the radical of the antibody T101 from which t phenolic groups of its tyrosines have been removed;

A' is as defined above, especially the radical of trichosanthin or trichokirin from which the thiol group of one of its cysteines has been removed; and W' is the group (c):

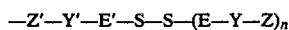

in which Z' is the oxygen of the phenolic hydroxyls involved in the coupling, Y is —CO—, E is the inert spacing structure —CH$_2$—CH$_2$— and n is zero.

Particular preference is given to the immunotoxins formed by one or more structures containing trichosanthin or trichokirin and an antibody P, which are represented by the statistical formula:

$$P'(W'—A')_m \qquad (III)$$

in which P', W' and A' are as defined above and m represents the number of groups belonging to the protein p which are involved in the coupling. The number m varies from 0.3 to 12, preferably from 0.5 to 10.

The expression "m varies from 0.3 to 12, preferably from 0.5 to 10" means that the value of m is a statistical value because the coupling does not take place homogeneously within the population of antibody molecules. The number m may therefore not be an integer.

The value of m depends especially on the antibodies used and more particularly on their molecular weight.

Thus, if a fragment Fab or Fab' is used as the starting antibody P, the value of m can vary between 0.3 and about 2; if a fragment F(ab')$_2$ is used, m can vary between 0.5 and about 4; for an antibody of the IgG type, the value of m will be between 0.5 and 6; finally, for an antibody IgM, the value of m can vary between 1 and 12.

It is preferable, however, for the degree of substitution on the antibody P to be such as to lead to a value of m which is not less than 0.5 and not more than 10.

More generally, the structures (I) and (II) above represent statistical formulae written in simplified form, as already explained.

Analogously, the formulae (IV), (V) and (VI) below are also statistical formulae—whenever n is 1—because the coupling reactants are prepared from populations of proteins P$_1$ and P$_2$ which all have exactly the same properties as those taken into account above for the antibody p, whether these proteins P$_1$ and P$_2$ themselves are the antibody P or the protein extracted from *Trichosanthes kirilowii*.

The immunotoxins having the statistical formula:

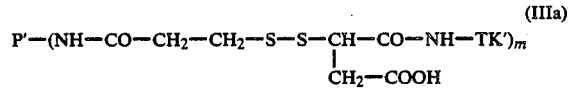

wherein P' and m are as above defined and TK' is the radical of the trichokirine as such, from which amino functions have been removed, and the immunotoxins having the statistical formula:

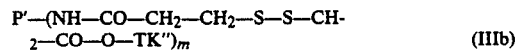

wherein P' and m are as hereinabove defined and TK" is the radical of the trichokirine as such, from which phenolic hydroxy functions have been removed, are particularly active.

According to another feature, the present invention relates to a process for the preparation of an immunotoxin having the structure (I) above, wherein a protein P$_1$, which is arbitrarily either optionally modified trichosanthin or trichokirin or an antibody or antibody fragment, carrying a least one free thiol group attached to the said protein P$_1$ directly or via spacing structure, is reacted, in aqueous solution and at room temperature, with a protein P$_2$ different from P$_1$, which is arbitrarily either optionally modified trichosanthin or trichokirin or an antibody or antibody fragment, carrying a group capable of coupling with the free thiol of the protein P$_1$ to form a thioether or disulfide bond.

According to a preferred feature, the present invention relates to a process for the preparation of an immunotoxin having the structure (II), in which P', W' and A' are as defined above, wherein a protein of the formula:

$$P_1'—(Z—Y—E)_n—SH \qquad (IV)$$

is reacted, in aqueous solution and at room temperature, with a protein of the statistical formula:

$$P_2'—Z'—Y'—E'—G \qquad (V)$$

in which P$_1$' and P$_2$' represent the radicals of the proteins P$_1$ and P$_2$ bonded to the groups belonging to the said proteins, or the radicals of one the protein P$_1$ or P$_2$ originating from the opening of the carbohydrate structures of the antibodies or antibody fragments or optionally of the protein A by reaction with periodic acid, Z, Z', Y, Y', E and E' are as defined above and G represents a group:

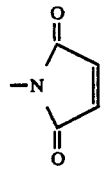

or a group —S—S—X, in which X is an activating group.

Therefore, both p and A are proteins which arbitrarily have:

(1) the thiol group or groups taking part in the coupling, and (2) one or more functional groups capable of reacting with the above thiol groups to form a disulfide or thioether bond.

According to the present invention, the said thiol groups and functional groups are those of the native proteins P or A or alternatively are introduced therein artificially.

For reasons of clarity, there now follows a description of the meaning of the symbols used to denote the above proteins or their radicals and of the expressions used to denote the various symbols.

The symbol P represents a protein chosen from any antibody or antibody fragment, any immunoglobulin or immunoglobulin fragment, or any molecule derived from these molecules by artificial modification of any one of their functional groups, including carbohydrate structures which they carry, with the proviso that the chosen protein is still capable of selectively recognizing a given antigen on the surface of the cells carrying this antigen, especially cancer cells.

The symbol A represents a protein which is the trichosanthin or the trichokirin, such as can be obtained directly from *Trichosanthes kirilowii*, or any molecule derived from these proteins by artificial modification of any functional group carried by these proteins, with the proviso that the chosen protein still has the property of inhibiting ribosomal protein synthesis in the eucaryotic cells, as can be demonstrated in an acellular study model.

The symbol P' represents a radical derived from the above protein P, as such or appropriately chemically modified, from which one or more of its own groups have been removed and in which other functional groups are optionally blocked.

The symbol A' represents a radical derived from the above protein A, as such or appropriately chemically modified, from which one or more of its own groups have been removed and in which other functional groups are optionally blocked.

The symbol $P_1$ represents one of the proteins A and P as defined above, which carries free thiol groups attached to the said protein directly or via a spacing structure.

The symbol $P_2$, which is different from $P_1$, represents one of the proteins A and P as defined above, which carries one or more functional groups capable of reacting with the free thiols.

The symbol $P_1'$ represents that radical of the protein $P_1$ which bears the groups belonging to the protein $P_1$, especially the groups SH (of the cysteine), $NH_2$ (in the terminal position of the protein or in the epsilon position of the lysines), OH (of the tyrosines) or COOH (of the aspartic and glutamic acids), or that radical of the protein $P_1$ which originates from the opening of the carbohydrate structures by reaction with periodic acid, when $P_1$ denotes an antibody or antibody fragment or optionally the protein A.

The symbol $P_2'$ represents that radical of the protein $P_2$ which bears the characteristic functional groups $NH_2$ (in the terminal position of the protein or in the epsilon position of the lysines), OH (of the tyrosines) or COOH (of the aspartic and glutamic acids).

For example, $P_1'$—SH represents the protein $P_1$ (which can arbitrarily be the antibody or antibody fragment P or trichosanthin or trichokirin) in which the SH groups of the cysteines are free and the other functional groups are optionally blocked.

In the same way, $P_1'$—CO— represents the protein $P_1$ in which the terminal carboxyl group or the carboxyl groups of its glutamic and aspartic acids are coupled with a group which artificially introduces an SH group.

Again, $P_2'$—NH— represents the protein $P_2$ (which can arbitrarily be the antibody or antibody fragment P or trichosanthin or trichokirin) in which the terminal amino group or the amino groups of its lysines are attached to a group capable of coupling with the thiol of the protein $P_1$.

The term "inert spacing structure", as used here for E and E', denotes a divalent organic radical which is inert towards the reactants used in the process, such as a straight-chain or branched alkylene group containing from 1 to 15 carbon atoms, which can contain one or more double bonds, can be interrupted by oxygen atoms or can be substituted by one or more inert functional groups such as methoxy groups, free or esterified carboxyl groups, dialkylamino groups or carbamate groups. The same term also denotes an arylene group containing from 6 to 15 carbon atoms, which can be substituted by one or more inert functional groups as indicated above for the alkylene group.

The expression "functional group capable of bonding covalently", as used here for Y and Y', denotes any groups capable of reacting with the groups belonging to the proteins $P_1$ and $P_2$ to give a covalent bond. Thus, for example the groups —CO— suitable functional groups capable of bonding with the free amines, the thiols and the phenolic hydroxyls of the proteins. Likewise, the group —NH— is a suitable functional group capable of bonding with the free carboxyl groups of the proteins. The group =N— is a suitable functional group capable of bonding with the two carbon atoms of the carbohydrate structures of the proteins $P_1$ or $P_2$ after oxidation with periodate ions, when $P_1$ or $P_2$ represents an antibody or antibody fragment or optionally the protein A.

The expression "group belonging to the proteins", as used here for Z, Z' and Z'', denotes the radicals originating from the characteristic groups of the amino acids forming the proteins $P_1$ and $P_2$, such as the oxygen atom originating from the hydroxyls of the tyrosine and possibly serine amino acids, the carbonyl group originating from the terminal carboxyl or the free carboxyls of the aspartic and glutamic acids, the —NH— group originating from the terminal amine of the proteins or the lysines, or the sulfur atom originating from the thiol of the cysteine. The same expression also denotes the group originating from the dialdehyde structure obtained after oxidation of one of the carbohydrate structures of the proteins $P_1$ or $P_2$ by treatment with periodate ions, when $P_1$ or $P_2$ represents an antibody or antibody fragment or optionally the protein A.

The term "activating radical", as used here for X, denotes a group bonded to an —S—S— bridge and capable of reacting with a free thiol to form a disulfide with the release of X—SH. Suitable activating radicals are pyridin-2-yl and pyridin-4-yl groups which are unsubstituted or substituted by one or more halogens or alkyl, carboxyl or alkoxycarbonyl radicals; the phenyl group which is unsubstituted or, preferably, substituted by one or more halogens or nitro, alkoxy, carboxyl or alkoxycarbonyl groups; or an alkoxycarbonyl group such as methoxycarbonyl.

The terms "alkyl" and "alkoxy" denote groups containing up to 5 carbon atoms.

The term "alkylene" denotes straight-chain or branched saturated aliphatic groups containing up to 10 carbon atoms, which can be substituted by one or more inert functional groups such as alkoxycarbonyl groups.

Trichosanthin is a ribosome-inactivating protein (RIP) extracted from the roots of *Trichosanthes kirilowii* and described in Nature 195 (1,2), 321 (1986). Extraction of the seeds of Trichosanthes kirilowii gives a novel and exceptionally powerful RIP which is different from trichosanthin. This novel RIP, called "trichokirin", has the following characteristics:

it is a glycoprotein with a molecular weight of 28,000±3,000 as determined by electrophoresis on polyacrylamide gel in the presence of SDS (sodium dodecyl-sulfate);

it has an isoelectric point $\geq 9$;

it has a content of neutral sugars of 1.1 to 1.5% by weight, including 0.3 to 1.2% of mannose;

it has the following amino acid composition, expressed as the number of residues per mol of protein ±20%:

| Lys : 17.3; | His : 1.1; | Arg : 6.7; | Asx : 22.8; |
|---|---|---|---|
| Thr : 18.9; | Ser : 23.5; | Glx : 21.6; | Pro : 8.0; |
| Gly : 16.0; | Ala : 21.1; | ½ Cys : 1.9; | |
| Val : 12.5; | Met : 3.05; | Ile : 15.8; | Leu : 24.3; |
| Tyr : 12.1; | Phe : 10.1; | Trp : n.d. | | where Asx is the aspartic acid and asparagine residues together, Glx is the glutamic acid and glutamine residues together, ½ Cys is the cystein residue of the native protein under the form of cysteic acid determined during the analysis and n. d. means "not determined"; and it has the following terminal amino sequence:

it has the following terminal amino sequence:
1                                               10
Asp—Val—Ser—Phe—Ser—Leu—Ser—Gly—Gly—Gly—
                          16
Thr—Ala—Ser—Tyr—Glu—Lys The amino acid composition is determined by heating at 105° C. for 24 hours under nitrogen, in the presence of 6N hydrochloric acid, 1% phenol and 1% 2-mercaptoethanol. The amino acids are converted to derivatives with phenyl isothiocyanate (PITC) in an alkaline medium. The phenylthiohydantions (PTH) so obtained are analyzed by reversed-phase HPLC. The cysteine was determined after oxidation of the protein with performic acid (J. Biol. Chem. 238, 235–237 (1963)).

The terminal amino sequence is determined with a microsequencer marketed by Applied Biosynthesis, starting from 5 nmol of protein solubilized in a 10% solution of acetic acid. The PITC amino acids are analyzed by reversed-phase HPLC.

Trichokirin is obtained by a process which comprises extracting the ground seeds of Trichosanthes kirilowii with water in the presence of a buffer at pH 6.5–7.5, removing the insoluble material, fractionating the crude extract by chromatography on a weakly acidic ion exchange resin using a buffer solution containing sodium chloride at a pH of 7.2–7.7 as the eluent, and isolating and purifying the fraction containing the inhibitor protein.

For example, the seeds of T. kirilowii, preferably decorated beforehand, are ground and extracted with water containing an electrolyte, for example sodium chloride, and a buffer, for example a phosphate buffer, at a pH around neutrality. The insoluble materials are removed, for example by centrifugation, and the low-molecular substances are removed from the solution by dialysis, for example against phosphate buffer The dialyzed extract is then fractionated, for example by chromatography on a weakly acidic ion exchange resin such as carboxymethyl cellulose. Elution can be carried out using a linear concentration gradient, for example a 0 to 0.3M aqueous solution of sodium chloride. Normally, 4 main peaks are eluted and peak IV, eluted by a sodium chloride concentration of 0.03 to 0.11M, contains the major part of the trichokirin.

The trichokirin can be purified by gel filtration, for example on a column of Sephadex (registered trademark).

Trichokirin can be coupled to antibodies or antibody fragments via an appropriate coupling agent by the process described above.

Trichokirin inhibits protein syntheses in a lyzate of reticulocytes with an $ID_{50}$ of 1.5–4 ng/ml. The effect is very much less on whole cells, the $ID_{50}$ varying from 7 to more than 100 μg/ml according to the cell examined.

Table 1 shows the effect of trichokirin on a variety of cells, especially the $ID_{50}$ (in μg/ml and $M.10^{-7}$) for the inhibition of protein synthesis; this was determined by applying the method described in J. Biol Chem. 259, 9359–9364 (1984).

TABLE 1

| Cell | $ID_{50}$ μg/ml | $M.10^{-7}$ |
|---|---|---|
| Human fibroblasts | 3.9 | 1.3 |
| TG cells | 7.5 | 2.5 |
| NB 100 cells (neuroblastoma) | 10.3 | 3.4 |
| JAR cells (choriocarcinoma) | 16.3 | 5.4 |
| HeLa cells | 45.0 | 15.0 |
| M 4039 (melanoma) | 9.9 | 3.3 |

The preparation of monoclonal antibodies directed against human cancer cells has been widely mentioned in the scientific literature and many of these antibodies are now commercially available.

The chemical coupling of trichosanthin or trichokirin with the antibody (or antibody fragment) can be effected by the process of the present invention using procedures which.

preserve the respective biological activities of the two components of the conjugate, namely the antibody and the trichosanthin or trichokirin, ensure that the process has a satisfactory reproducibility and a good coupling yield, make it possible to control the value of the toxin-to-antibody ratio in the conjugate obtained, and lead to a stable and water-soluble product.

Among the procedures corresponding to these characteristics, preference must be given to those which involve one or more thiol groups for forming the bond between the 2 proteins. In fact, these thiol groups are particularly suitable for forming either disulfide bonds or thioether bonds, both of which satisfy the general conditions above. These procedures are disclosed in U.S Pat. No. 4,340,,535 and in European Patent No. 189,111.

In general, in order to carry out the coupling reactions between proteins successfully and to eliminate disordered crosslinkings in particular, it is important for one of the proteins to be coupled, and one only, to carry the thiol or thiol groups to be used, while only the other protein carries one or more groups capable of reacting with the thiols in an aqueous medium having a pH of between 5 and 9, and at a temperature not exceeding 30° C., to produce a stable and clearly defined covalent bond.

The characteristics of the proteins $P_1$ and $P_2$ used as starting materials are illustrated in detail below. The spacing structure E can be replaced by the preferred structures R to $R_8$, which are only given as examples.

THE PROTEIN $P_1$

As this protein is in all cases the one carrying the thiol group or groups which will take part in the coupling, the situation which arises varies according to the nature of this protein $P_1$.

(A) The protein $P_1$ carries, in the natural state, one or more thiol radicals which can be used to permit coupling with the protein $P_2$; this is particularly the case if the protein $P_1$ is the antibody fragment known as F(ab)', as conventionally obtained by the limited proteolysis of the antibody in the presence of pepsin, followed by reduction of the disulfide bridge (or bridges) between high-molecular chains.

This is also the case if the protein $P_1$ is trichosanthin or trichokirin or a derivative of one of these toxins in which at least one of the thiol groups carried by the cysteine residues of the native toxin is free and accessible for chemical coupling.

In all cases, the protein $P_1$ carrying its natural thiol group (or groups) can be used in this state for the coupling step.

(B) The protein $P_1$ does not carry, in the natural state, thiol radicals which can be used to permit coupling with the protein $P_2$:

this is especially the case if the protein $P_1$ is a native immunoglobulin, a whole antibody or an antibody fragment, especially one of the fragments commonly called F(ab)'$_2$ or F(ab);

another case in which the protein $P_1$ does not carry, in the natural state, a thiol group which can be used for coupling is the case where this protein $P_1$ is trichosanthin or trichokirin in which each of the cysteine residues is either blocked by alkylation or inaccessible for chemical modification.

In all cases, it will then be appropriate artificially to introduce into such molecules one or more thiol groups capable of permitting coupling.

Three types of reaction can preferably be used for the introduction of thiol groups:

1—The first type of reaction is with S-acetylmercaptosuccinic anhydride, which is capable of acylating amine groups of the protein. It will then be possible to free the thiol groups by reaction with hydroxylamine to remove the acetyl protecting radical. In the manner already described (Archives of Biochemistry and Biophysics, 119, 41–49, (1967)). It will even be possible, in the case where the thiol group (or groups) thus introduced in the protected form are subsequently to react with an activated mixed disulfide radical, to dispense with the prior deprotection by means of hydroxylamine; in fact, the reaction for formation of the disulfide bond using the reactants forming the subject of the present invention takes place just as well with the S-acetyl radical as with the free thiol.

Other methods described in the scientific literature can also be used to introduce thiol groups into the protein to be modified.

One particularly advantageous modified protein $P_1$ is a S-acetylmercaptosuccinoyl-trichlkirine obtained by treating trichokirin with S-acetylmercaptosuccinic anhydride, another being the corresponding mercaptosuccinoyl derivative prepared by reacting hydroxylamine with the S-acetyl derivative.

This modified trichokirin can be represented by the formula:

$$TK^*-(CO-CH-S-Q)_p$$
$$\qquad\qquad\; |$$
$$\qquad\quad\; CH_2COOH$$

in which TK* represents the trichokirin radical, Q represents hydrogen or the acetyl group and p can vary between 0.2 and 3, preferably between 0.4 and 1.

2—The second type of reaction consists in reacting the protein via its carboxyl groups with a symmetrical diamine molecule having a disulfide bridge, of the formula:

$$H_2N-R_1-S-S-R_1-NH_2$$

in which $R_1$ is an aliphatic group containing from 2 to 5 carbon atoms.

The reaction is preferably carried out with cystamine $[R_1=-(CH_2)_2-]$ in the presence of a coupling agent such as a carbodiimide and especially a water-soluble derivative like 1-ethyl-3-(3-dimethylaminopropyl)carbodiimide, and leads to the formation, depending on the stoichiometries used, of one of the following derivatives or a mixture of both:

$$P_1'-CO-NH-R_1-S-S-R_1-NH_2 \qquad (Ia)$$

$$P_1'-CO-NH-R_1-S-S-R_1-NH-CO-P_1' \qquad (Ib).$$

A reaction product of this type can then be used in two ways:

(a) If, in the formulae Ia and Ib, the protein $P_1'$ is the radical of protein $P_1$ which is trichosanthin or trichokirin or one of their derivatives, the reaction medium obtained is subjected, without fractionation, to the action of a reducing agent such as 2-mercaptoethanol, which gives a single protein derivative of the general formula:

$$P_1'-CONH-R_1-SH.$$

The product thus obtained is then purified by dialysis or gel filtration.

(b) If, in the formulae Ia and Ib, the radical $P_1'$ is that radical of the protein $P_1$ which consists of an antibody or one of its fragments, the reaction medium obtained will be used as such for the coupling, in which case a thiol/disulfide exchange method will be used, for example the one described by Gilliland and Collier (Cancer Research, 40, 3564, (1980)).

3—The third type of reaction consists in using carbohydrate units, which are present in the natural state in the antibodies, in order to attach the radical carrying the thiol which it is proposed to introduce. The protein is then subjected to oxidation with periodate ions in order to create aldehyde groups on the carbohydrate units. The reaction is stopped by the addition of a reagent which consumes the remaining periodate, for example an excess of ethylene glycol, and the by-products are removed by dialysis or any other appropriate treatment. The product obtained is treated with a symmetrical diamine molecule having a disulfide bridge, of the general formula:

$$H_2N-R_1-S-S-R_1-NH_2$$

in which $R_1$ is an aliphatic group containing from 2 to 5 carbon atoms. The addition products formed are then reduced to secondary or tertiary amines by reaction with a suitable metal hydride, especially sodium borohydride. The reaction is preferably carried out with cystamine [$R_1 = -(CH_2)_2-$] and leads to the formation, depending on the stoichiometries used, of one of the following derivatives or a mixture of both:

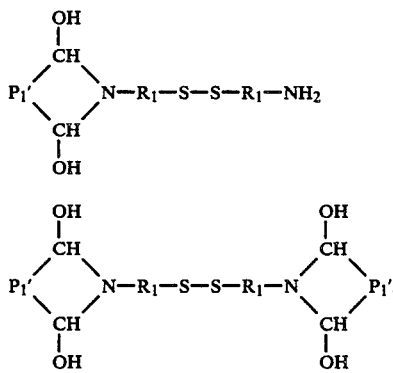

The reaction medium may then be treated exactly as indicated above for the products characterized by the structures Ia or Ib in which $P_1'$ represents an antibody or antibody fragment.

In the last two types of reaction, described above, for the artificial introduction of thiol groups (the types using a symmetrical diamine disulfide reactant), the protein $P_1$ used preferably possesses no free SH groups.

In the case of antibodies or antibody fragments and, more generally, all the substances of the first group, as defined previously, which do not possess naturally free SH groups, it will be appropriate to carry out a reductive methylation, for example by the method of MEANS and FEENEY; in this way, it is usually possible to introduce several dozen methyl radicals per mol of antibody without modifying its capacity to selectively recognize an antigen on the surface of the cells carrying this antigen.

THE PROTEIN $P_2$

This protein is in all cases the one which carries one or more functional groups capable of reacting with the thiols of the protein $P_1$ to form either a disulfide or a thioether bond. These functional groups, which are always introduced artificially into the protein $P_2$, differ according to whether it is desired to effect coupling by a disulfide bond or by a thioether bond and are chosen as indicated below.

(A) The disulfide bond

In this case, the preparation of the conjugate can be represented by the equation:

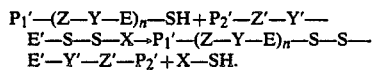

The protein $P_2'$ substituted by an activated sulfur atom is obtained from the protein $P_2$ itself or from the correctly protected protein $P_2$ by substitution with the aid of a reagent which itself carries an activated sulfur atom, according to the equation:

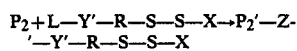

in which:
$P_2$ denotes the protein to be substituted and

L—Y' represents a group permitting the covalent attachment of the reagent to the protein.

The functional group L—Y' is a group capable of bonding covalently with any one of the groups carried by the side chains of the constituent amino acids of the protein to be substituted. Among these groups, the following will be singled out in particular:

(a) the amine end groups of the peptide chains or the amine side groups of the lysyl radicals contained in the protein.

In this case, L—Y' can represent especially:
a carboxyl group which can bond to the amine groups of the protein in the presence of a coupling agent such as a carbodiimide and especially a water-soluble derivative like 1-ethyl-3-(3-dimethylaminopropyl)carbodiimide;

a carboxylic acid chloride which is capable of reacting directly with the amine groups to acylate them;

a so-called "activated" ester such as an ortho- or para-nitrophenyl or -dinitrophenyl ester, or alternatively an N-hydroxysuccinimide ester, which can react directly with the amine groups to acylate them;

an internal anhydride of a dicarboxylic acid, for example succinic anhydride, which reacts spontaneously with the amine groups to create amide bonds; or an imidoester group:

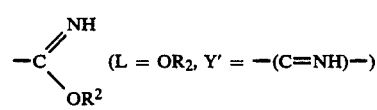

in which $R_2$ is an alkyl group, which reacts with the amine groups of the protein $P_2$ according to the equation:

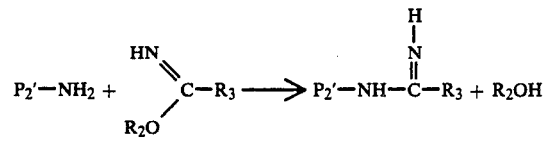

in which $R_3$ represents the group —R—S—SX;

(b) the phenol groups of the tyrosyl radicals contained in the protein.

In this case, L—Y' can represent especially an imidazol-1-ylcarbonyl group, which reacts with the phenol groups of the protein according to the equation:

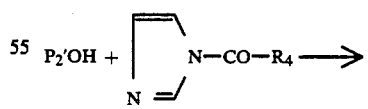

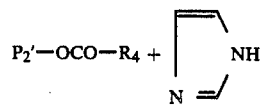

in which the imidazol-1-yl is L, the CO group is Y' and $R_4$ is the group —R—S—S—X.

The radical —S—S—X denotes an activated mixed disulfide capable of reacting with a free thiol radical. In particular, in this mixed disulfide, X can denote a pyridin-2-yl or pyridin-4-yl group optionally substituted by one or more alkyl, halogen or carboxyl radicals. X can also denote a phenyl group preferably substituted by one or more nitro or carboxyl groups. Alternatively, X can represent an alkoxycarbonyl group such as the methoxycarbonyl group.

The radical R denotes the spacing structure (indicated as E in the general formula II above) capable of carrying the substituents Y' and S—S—H simultaneously, it must be chosen so as not to contain groups capable of interfering, during the subsequent reactions, with the reactants used and the products synthesized. In particular, the group R can be a group —(CH$_2$)$_n$—, n being between 1 and 10, or alternatively a group:

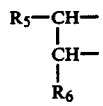

in which R$_6$ denotes hydrogen or an alkyl group having from 1 to 8 carbon atoms and R$_5$ denotes a substituent which is inert towards the reactants to be used subsequently, such as a carbamate group:

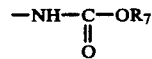

in which R$_7$ denotes a linear or branched alkyl group having from 1 to 5 carbon atoms, especially the tert-butyl group.

The reaction of the compound L—Y'—R—S—S—X with the protein P$_2$ is carried out in a homogeneous liquid phase, most commonly in water or a buffer solution. If necessitated by the solubility of the reactants, a water-miscible organic solvent can be added to the reaction medium at a final concentration which can reach 20% by volume in the case of a tertiary alcohol, such as tertiary butanol, or 10% by volume in the case of dimethylformamide or tetrahydrofuran.

The reaction is carried out at room temperature for a time varying from a few minutes to a few hours, after which the low-molecular products, and in particular the excess reactants, can be removed by dialysis or gel filtration. This process usually makes it possible to introduce between 1 and 15 substituent groups per mol of protein.

When using such compounds, the coupling with the protein P$_1$ is carried out by bringing the two proteins together in an aqueous solution having a pH of between 6 and 8, at a temperature not exceeding 30° C., for a time varying from 1 hour to 24 hours. The aqueous solution obtained is dialyzed, if appropriate, to remove the low-molecular products, and the conjugate can then be purified by a variety of known methods.

(B) The thioether bond

In this case, the preparation of the conjugate consists in reacting P$_1$'—(Z—Y—E)$_n$—SH with the protein P$_2$ into which one or more maleimide radicals have been introduced beforehand.

The reaction is then represented by the following equation, which is given as an example:

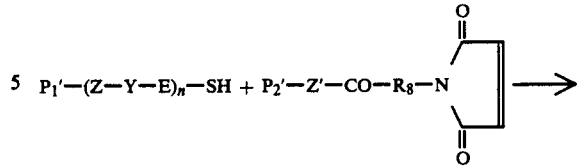

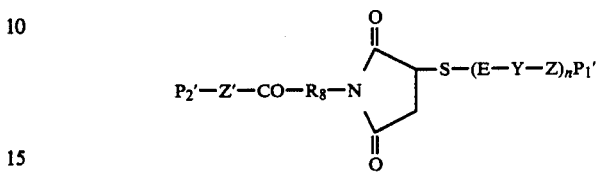

in which:

R$_8$ represents an aliphatic or aromatic spacing structure containing from 1 to 15 carbon atoms, which is inert towards the reactants to be used subsequently, and Z' represents groups which can vary according to the type of functional group of the protein P$_2$ involved in the coupling Thus, Z'=oxygen in the case of an ester on the phenol of a tyrosyl residue: Z'=NH in the case of the coupling of an activated carboxyl group with an amine group of the protein; or Z'=NH—CH$_2$ in the case of the reaction of a chloromethyl ketone with an amine group of the protein.

The protein P$_2$ substituted by the maleimide group or groups is obtained from the protein P$_2$ itself, or the correctly protected protein P$_2$, by substitution of suitable groups of the protein with the aid of a reagent which itself carries the maleimide group. Among these suitable groups, the following will be singled out in particular:

(a) the amine end groups of the peptide chains or the amine side groups of the lysyl residues contained in the protein. In this case, the reagent carrying the maleimide radical can be:

either a reagent of the general formula:

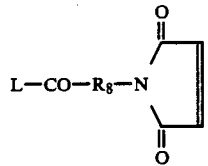

in which L-CO- represents:

either a carboxyl group, in which case the reaction is carried out, after activation of the carboxyl group, in the presence of a coupling agent such as a carbodiimide and especially a water-soluble derivative such as 1-ethyl-3-(3-dimethylaminopropyl)carbodiimide, or a so-called "activated" ester such as an ortho- or para-nitrophenyl or -dinitrophenyl ester, or alternatively an N-hydroxysuccinimide ester, which reacts directly with the amine groups to acylate them.

The preparation of such reagents is described especially in Helvetica Chimica Acta 58, 531–541 (1975). Other reagents in the same class are commercially available.

or a reagent of the general formula:

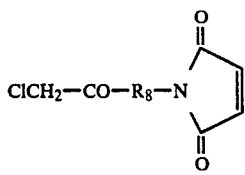

which is capable of reacting with the amine groups of the protein $P_2$ according to the equation:

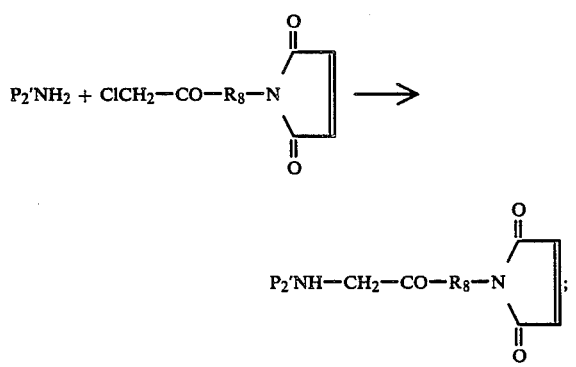

(b) the phenol groups of the tyrosyl radicals contained in the protein. In this case, the reagent carrying the maleimide radical can be a reagent of the general formula:

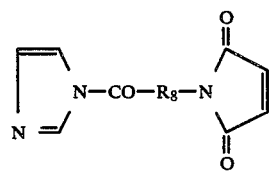

which reacts with the phenol groups of the protein according to the equation:

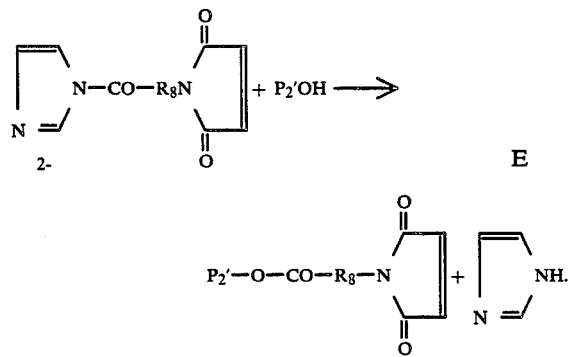

The reaction of the maleimide-carrying reagents with the protein $P_2$ is carried out in a homogeneous liquid phase, most commonly in water or a buffer solution. If necessitated by the solubility of the reactants, a water-miscible organic solvent can be added to the reaction medium at a final concentration which can reach 20% by volume in the case of a tertiary alcohol, such as tertiary butanol, or 10% by volume in the case of dimethylformamide or tetrahydrofuran.

The reaction is carried out at room temperature for a time varying from a few minutes to a few hours, after which the low-molecular products, and in particular the excess reactants, can be removed by dialysis or gel filtration. This process usually makes it possible to introduce between 1 and 15 substituent groups per mol of protein.

When using such compounds, the coupling with the protein $P_1$ is carried out by bringing the two protein derivatives together in an aqueous solution having a pH of between 6 and 8, at a temperature not exceeding 30° C., for a time varying from 1 hour to 24 hours. The solution obtained is dialyzed, if appropriate, to remove the low-molecular products, and the conjugate can then be purified by a variety of known methods.

Among the compounds of the present invention, those which are particularly suitable are the compounds of the formula (II) in which W' represents one of the groups (a), (b), (c) and (d) above in which E and E' represent a group —$(CH_2)_p$—, p being an integer from 2 to 7, or a group:

$$-\underset{\underset{CH_2COOH}{|}}{CH}-$$

Thus, particularly valuable protein derivatives are represented by the statistical formula:

$$P_2''—O—CO—E—G \qquad (VI)$$

in which:
  $P_2'$ represents the radical of a protein selected from the group comprising:
    any antibody or antibody fragment, any immunoglobulin or immunoglobulin fragment or any molecule derived from these molecules by artificial modification of any one of their functional groups; and
    trichosanthin or trichokirin or any molecule derived from the said proteins by artificial modification of any one of their functional groups,
  the said radical being the protein from which one or more phenolic hydroxyl groups of the tyrosines have been removed;
  the oxygen atom is that belonging to the phenolic hydroxyl groups missing from the radical $P_2''$; and
  E and G are as defined above.

Particular preference is given to the compounds of the E represents formula—($\overline{CH}_2$ )$_p$—, in which p is an integer from 2 to 7, or a group:

$$-\underset{\underset{CH_2COOH}{|}}{CH}-$$

and G is a group of the structure —S—S—X, in which X is an activating radical chosen from the pyridin-2-yl and pyridin-4-yl groups which are unsubstituted or substituted by one or more halogens or alkyl, carboxyl or alkoxycarbonyl radicals, the phenyl group which is unsubstituted or substituted by one or more halogens or nitro, alkoxy, carboxyl or alkoxycarbonyl groups, or an alkoxycarbonyl group.

The products of the formula (VI) are prepared by reacting a product of the formula:

$$P_2''—OH$$

in which $P_2'$ is as defined above and the hydroxyl group is the phenolic hydroxyl missing from the tyrosines of the radical $P_2'$, with a compound of the formula (VII) below:

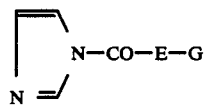

(VII)

at a temperature of 10° to 40° C., in an aqueous solvent optionally containing a water-miscible organic solvent, for example an ether solvent like dioxane or tetrahydrofuran.

The examples which follow provide a clearer understanding of the invention without limiting its scope.

The monoclonal antibody AT15E is directed against the antigen Thy 1.2 of murine lymphocytes. This antibody is the one described in Journal of Immunology 122, 2491-8 (1979) and has been obtained from the hybridoma described in Hybridoma 1(1), 13-17 (1981).

In the examples, trichokirin is denoted by the abbreviation TK.

EXAMPLE 1

ISOLATION OF TRICHOKIRIN (A) Crude extract

Seeds of Trichosanthes kirilowii (1.2 kg) are ground in an Ultraturrax apparatus with 8 volumes of a 0.14 M solution of sodium chloride containing 5 mM phosphate buffer, pH 7.5. Extraction is continued overnight at 4° C., with magnetic stirring.

After removal of the coarse residues, the extract is centrifuged at 10,000 g for 45 minutes at 0° C. The supernatant is decanted in the cold to remove the solidified fats, after which the proteins are precipitated by the addition of ammonium sulfate up to saturation point. After centrifugation as indicated above, the precipitated product is resuspended in 1 liter of a 0.14 M aqueous solution of sodium chloride containing 5 mM phosphate buffer, pH 7.5. The undissolved product is removed by centrifugation under the same conditions as above. The supernatant is transferred to a column of Sephadex G 25 coarse (95 cm × 10 cm), equilibrated with 5 mM phosphate buffer, pH 7.0, at room temperature, and eluted at a rate of 3 l/hour. The first peak is collected.

(B) Ion exchange chromatography

The combined extracts from 2 operations (originating from 2.4 kg of seeds) are treated with sodium chloride up to a final concentration of 30 mM and transferred to a column of CM-Sepharose Fast Flow (17.5 cm × 5 cm), equilibrated with 30 mM phosphate buffer, pH 7.0. The non-fixed product is eluted with the same buffer. The bound protein is eluted by a gradient containing from 30 to 110 mmol/l of sodium chloride in the same phosphate buffer (volume 20 liters). 400 ml fractions are collected at a rate of 1.2 liters per hour. The absorbance at 280 nm and the conductivity of the eluate are monitored. The fractions showing an inhibitory activity against protein synthesis are combined (3.6 l) and acidified to pH 5.8 with acetic acid. The solution is transferred to a column of S-Sepharose Fast Flow (6.6 cm × 5 cm), equilibrated with 10 mM sodium acetate buffer, pH 4.5. After washing with the same buffer, the fixed protein is eluted with 20 mM phosphate buffer, pH 7.5, containing 0.5 M sodium chloride.

The fraction corresponding to the peak containing the protein (200 ml) is collected, dialyzed against 3 times 50 l of distilled water and then lyophilized to give 380 mg of trichokirin.

(C) Gel filtration

The trichokirin obtained above is dissolved in 50 ml of a 0.14 M solution of sodium chloride. An insoluble material is removed by centrifugation at 20,000 g for 30 minutes. The supernatant is transferred to a column of Sephadex G 50 coarse (95 cm × 5 cm), equilibrated with 5 mM phosphate buffer, pH 7.0, at 4° C. Elution is carried out at a rate of 60 ml/hour. The solution corresponding to the peak containing the protein is collected, dialyzed and lyophilized as indicated above.

This gives 267 mg of purified trichokirin.

EXAMPLE 2

S-ACETYLMERCAPTOSUCCINOYL-TRI-CHOKIRIN AND MERCAPTOSUCCINOYL-TRICHOKIRIN 100 microliters of a solution of S-acetylmercaptosuccinic anhydride (SAMSA) containing 10.5 mg/ml (60.33 micromol/ml) in dimethylformamide are added to a solution of 5.8 mg of trichokirin (0.215 micromol) in 6 ml of 125 mM phosphate buffer, pH 7 (i.e. 0.973 mg/ml, about 0.036 micromol/ml). Incubation takes one hour, after which the reaction medium is purified by dialysis against 125 mM phosphate buffer, pH 7, to remove the excess reagent. This gives 5.7 ml of a solution of S-acetylmercaptosuccinoyl-trichokirin containing 0.948 mg/ml. Reaction with hydroxylamine by ELLMAN's method containing 0.7 free SH group per mol of trichokirin (spectrophotometric analysis). When examined by polyacrylamide gradient electrophoresis, this modified protein shows a single band with a molecular weight of the order of 28,000±3000, which is identical to that of the native protein.

EXAMPLE 3

CONJUGATE OBTAINED BY REACTING THE ANTIBODY AT15E (ANTI-THY 1.2) WITH MERCAPTOSUCCINOYL-TRICHOKIRIN (A) Preparation of the modified antibody AT15E The antibody AT15E is a monoclonal antibody directed against the antigen Thy 1.2 of murine lymphocytes. This antibody is the one described in Journal of Immunology 122, 2491-8 (1979) and has been obtained from the hybridoma described in Hybridoma 1(1), 13-17 (1981).

25 microliters of a solution of N-succinimidin-3-yl 3-(pyridin-2-yldisulfanyl)propionate containing 5.5 mg/ml in ethanol are added to 3.7 ml of a solution of antibody A15E containing 3.55 mg/ml (i.e. 0.087 micromol) in 0.1 M borate buffer, pH 8.8.

Incubation takes 30 minutes and the excess reagent is then removed by dialysis against 125 mM phosphate buffer, pH 7. After dialysis, the protein solution is centrifuged to give 3.3 ml of a solution containing 3.4 mg/ml. By spectrophotometric analysis at 343 nm of the pyridine-2-thione released by exchange with 2-mercaptoethanol, it is found that the antibody obtained carries 3.2 activated mixed disulfide groups per mol of antibody.

(B) Preparation of the immunotoxin (conjugate)

5 ml of the solution of modified trichokirin obtained above (i.e. 0.183 micromol) are added to 1.9 ml of the solution of activated antibody obtained above (i.e. 0.043 micromol) and the mixture is incubated for 20 hours at 25° C. in the presence of 350 microliters of a molar solution of hydroxylamine hydrochloride. The solution is centrifuged and then purified by filtration on a column of Sephadex G200, the optical density of the effluent being measured at 280 nm. Combination of the fractions containing both the antibody and the TK gives 20 ml of a solution of immunotoxin containing 0.215 mg/ml (i.e. 4.3 mg). This solution contains 0 045 mg/ml of modified trichokirin coupled with the antibody.

The average degree of coupling in this preparation is 1.5 TK per mol of antibody. The conjugate so obtained has the above formula (IIIa) wherein P′ the radical of antibody AT15E devoid of amino functions and m is 1.5.

IMMUNOTOXIN ACTIVITY TESTS

One of the properties of trichokirin is to inhibit protein synthesis in eucaryotic cells. The tests performed are therefore tests for the inhibition of protein synthesis:
either on an acellular model
or on a cell model.

(A) The acellular model

The in vitro protocol uses appropriately complemented subcellular fractions of rat liver capable of incorporating $^{14}C$-phenylalanine in the presence of an artificial messenger RNA: polyuridylic acid.

The procedure employed for preparing the subcellular fractions and measuring the incorporation of $^{14}C$-Phenylalanine is an adaptation of the method described in Biochimica et Biophysica Acta 312, 608–615 (1973), using both a microsomal fraction and a cytosol fraction of the rat hepatocytes. The sample containing the trichokirin is introduced in the form of a solution appropriately diluted in a 50 mM tris-HCl buffer, pH 7.6, containing 0.2% of 2-mercaptoethanol and 15 micrograms/ml of bovine serum albumin. The count data are used to calculate, relative to a reference medium without inhibitor, the percentage inhibition of the incorporation of $^{14}C$-phenylalanine for each reaction medium.

The values obtained together make it possible to determine the concentration of trichokirin (or $IC_{50}$) which inhibits the incorporation of $^{14}C$-phenylalanine by 50% under the experimental conditions. Thus, the $IC_{50}$ of native trichokirin was found to be equal to $7.10^{-11}$ M, while that of the modified trichokirin was found to be equal to $8$–$10.10^{-11}$ mol/liter. Therefore, the modification does not cause a significant loss of activity of the trichokirin.

(B) Specific cytotoxicity of the trichokirin immunotoxin on a cell model

The biological activity of trichokirin is to inhibit protein synthesis in eucaryotic cell systems. The technique employed uses a cell model in which the effect of the substances studied on the incorporation of $^{14}C$-leucine into cancer cells in culture is measured. The cells used belong to the T2 cell line derived from a T murine leukemia expressing the surface antigen Thy 1.2. The cells are incubated in the presence of different concentrations of the substance to be studied, and then, when incubation has ended, the degree of incorporation of $^{14}C$-leucine by the cells treated in this way is measured.

This measurement is carried out by a technique adapted from the procedure described in Journal of Biological Chemistry 249(II) 3557–3562, (1974), using the tracer $^{14}C$-leucine to determine the degree of protein synthesis. The radioactivity incorporated is determined here on the whole cells isolated by filtration.

On the basis of these determinations, it is possible to draw the dose/effect curves, plotting, on the abscissa, the molar concentration of trichokirin in the substances studied, and, on the ordinate, the incorporation of $^{14}C$-leucine expressed as a percentage of the incorporation by control cells in the absence of any substance affecting protein synthesis.

It is thus possible to determine, for each substance studied, the concentration which causes a 50 % inhibition of the incorporation of $^{14}C$-leucine, or "50% inhibitory concentration" ($IC_{50}$). Table 2 shows the $IC_{50}$ values obtained in the same experiment with the trichokirin immunotoxin on the one hand and uncoupled trichokirin on the other.

TABLE 2

| Product | 50% inhibitory concentration |
|---|---|
| Trichokirin IT | $2 \times 10^{-10}$ M |
| Trichokirin | $2 \times 10^{-6}$ M |

It can be seen that the trichokirin IT has a strong cytotoxic activity which is more than 10,000 times higher than that of uncoupled trichokirin.

EXAMPLE 4

CONJUGATE OBTAINED BY REACTING THE ANTIBODY AT5E (ANTI-THY A.2) WITH TRICHOKIRINE 3-(PYRIDIN-2-YLDISULFANYL)PROPIONATE

(A) Preparation of the modified antibody 50 microliters of a solution of 8-acetylmercaptosuccinic anhydride (SAMSA) containing 35 mg/ml in dimethylformamide are added to 20.1 mg of a solution of antibody AT15E containing 4.02 mg/ml (i.e. 0.134 micromol). The reaction medium is incubated for 2 hours 30 minutes at 10° C. and then purified by dialysis against 125 mM phosphate buffer, pH 7, to remove the excess reagent.

This gives 4.5 ml of a solution containing 3.7 mg/ml.

200 microliters of a 1 M solution of hydroxylamine hydrochloride are added to 4.5 ml of this solution of antibody. After incubation for 2 hours at 25° C., the reaction medium is purified by dialysis against 125 mM phosphate buffer, pH 7, to remove the hydroxylamine.

By spectrophotometric analysis of the SH groups released by Ellman's method, it is found that the IgG obtained carries 3.8 SH groups per mol of antibody.

(B) Preparation of the coupling reagent

The coupling reagent is the imidazolide derived from 3-(pyridin-2-yldisulfanyl)propionic acid, for which the method of preparation has already been described in European Patent Application No. 169,111.

215 mg of 3-(pyridin-2-yldisulfanyl)propionic acid are dissolved in 0.5 ml of tetrahydrofuran. 203 mg of CDI (carbonyldiimidazole) are added to this solution. The mixture is stirred for 15 min at 25° C. An evolution of $CO_2$ gas is observed. The reaction medium is used directly and immediately without purification.

(C) Modification of the trichokirin 18.5 microliters of the solution of the coupling reagent in THF to 5 mg of TK in 5 ml of 125 mM phosphate buffer, pH 7 (i.e. 0.185 micromol). The mixture is incubated for 15 minutes at 25° C. and the reaction medium is then purified by dialysis against 125 mM phosphate buffer, pH 7, to remove the excess reagent. After centrifugation (15 min at 15,000 rpm), 4.4 ml of a solution of modified TK containing 0.94 mg/ml are obtained.

By spectrophotometric analysis at 343 nm of the pyridine-2-thione released by exchange with 2-mercaptoethanol, it is found that the TK obtained carries 0.6 activating group per mol of TK.

(D) Preparation of the immunotoxin 1.8 ml of the solution of TK (i.e. 0.063 micromol) are added to 0.5 ml of the solution of antibody obtained above (i.e. 0.012 micromol). The mixture is incubated for 20 hours at 30° C.

The reaction medium is purified by passage through an ACA44 column marketed by IBF-Rhone-Poulenc, elution being followed by measurement of the optical density of the effluent at 280 nm. Elution is carried out using PBS buffer (saline phosphate) to give 6.6 ml of a solution of immunotoxin containing 0.146 mg/ml (i.e. 0.966 mg). This solution contains 0.022 mg/ml of modified TK. The average degree of coupling of this preparation is one TK per mol of antibody. The conjugate so obtained has the above formula (IIIb) wherein P' is the radical of antibody AT15E from which amino functions have been removed and m is 1.

(E) Immunotoxin activity test

The cytotoxic activity of the immunotoxin is measured by the same procedure as that described in Example 3.

Table 3 shows the $IC_{50}$ values obtained in the same experiment with, on the one hand, the trichokirin immunotoxin conjugated by the tyrosines, and, on the other hand, uncoupled trichokirin.

TABLE 3

| Product | 50% inhibitory concentration |
|---|---|
| Trichokirine (IT) | $3 \times 10^{-10}$ M |
| Trichokirin | $3 \times 10^{-6}$ M |

It can be seen that the IT prepared by conjugating the anti-Thy 1.2 antibody with trichokirin by its tyrosine residues has a very strong cytotoxic activity which is 10,000 times higher than that of uncoupled trichokirin.

EXAMPLE 5

CONJUGATE OBTAINED BY REACTING THE ANTI-THY 1.2 ANTIBODY AT15E SUBSTITUTED BY AN ACTIVATED DISULFIDE GROUP WITH TK INTO WHICH A THIOL HAS BEEN INTRODUCED (A) Preparation of the modified TK 168 microliters of an aqueous solution of 3,3-dimethyldithio-bis-propionimidate (DTBP) are added to a solution of 7.25 mg of TK in 8.5 ml of 125 mM phosphate buffer, pH 7 (i.e. 0.853 mg/ml). Incubation takes 1 hour at 28° C. and the reaction medium is then purified by dialysis against 125 mM phosphate buffer, pH 7, to remove the excess reagent. The disulfide bridge of the DTBP attached to the protein is then reduced with 2-mercaptoethanol (at a final concentration of 1 percent for 1 hour at 30° C.).

Dialysis against 125 mM phosphate buffer, pH 7, is then continued as before. After centrifugation, 7 ml of a solution of modified TK containing 0.794 mg/ml are obtained. 0.6 free SH group per mol of protein can be determined in this product by Ellman's method.

(B) Preparation of the modified antibody 21 microliters of a solution containing 5.2 mg of N-succinimidin-3-yl 3-(pyridin-2-yldisulfanyl)propionate dissolved in 1 ml of ethanol are added to 3 ml of a solution of antibody AT15E containing 4 mg/ml in 0.1 M borate buffer, pH 8.8. Incubation takes ½ hour at 28° C. and the excess reagent is then removed by dialysis against 125 mM phosphate buffer, pH 7. After dialysis, the protein solution is centrifuged to give 2.3 ml of a solution containing 3 mg/ml.

By spectrophotometric analysis at 343 nm of the pyridine-2-thione released by exchange with 2-mercaptoethanol, it is found that the antibody obtained carries 3.8 activated mixed disulfide groups per mol of antibody.

(C) Preparation of the immunotoxin 5.4 ml of the solution of modified TK obtained in (A) are added to 2 ml of the solution of modified antibody obtained above and the mixture is incubated for 6 hours at 28° C. The solution is centrifuged and then purified by filtration on a column of Sephacryl S200 HR, the optical density of the effluent being measured at 280 nm.

Combination of the fractions containing both the antibody and the TK gives 14 ml of a solution of immunotoxin containing 0.09 mg/ml. The average degree of coupling in this preparation is 1.5 mol of TK per mol of antibody. The conjugate so obtained has the above formula (III) wherein:

P' is the radical of antibody AT15E from which amino functions have been removed W' is the group $-Z'-Y'-E'-S-S(E-Y-Z)_n$ wherein z' is NH;

Y' is CO:

E' is $-CH_2-CH_2-$

E' is $-CH_2CH_2-$

Y is $-C=NH$ n is 1

A' is the radical of the trichokirine from which the amino function have been removed; m is 1.5.

(D) Immunotoxin activity test

The activity of the immunotoxin is measured by the same procedure as that described in Example 3. Table 4 shows the $IC_{50}$ values obtained in the same experiment with, on the one hand, the trichokirin immunotoxin prepared as above, and, on the other hand, uncoupled trichokirin.

TABLE 4

| Product | 50% inhibitory concentration |
|---|---|
| Trichokirine (IT) | $8 - 10 \times 10^{-11}$ M |
| Trichokirin | $3 \times 10^{-6}$ M |

It can be seen that the IT has a very strong cytotoxic activity which is 30,000 times higher than that of uncoupled trichokirin.

This novel class of immunotoxins can be used to treat cancerous or non-cancerous diseases where the target cells to be destroyed would be recognized by the antibody or antibody fragment used to prepare the immunotoxin. The optimum modes of administration and the duration of the treatment will have to be determined in each case according to the subject and the nature of the disease to be treated.

The physiologically active products of the invention can be formulated for administration by any suitable method. Usually, the active principle will be administered by injection and will be formulated in an apyrogenic sterile liquid, preferably water, which can contain physiologically acceptable salts, such as buffers or sodium chloride, so as to give an isotonic solution.

For an antitumoral treatment, the daily dose of trichosanthin or trichokirin as a conjugate is preferably between 1 and 100 mg and advantageously from 5 to 50 mg, for example about 10 mg.

The dosage units containing trichosanthin or trichokirin in the form of a conjugate, for example ampoules for injection, will therefore usually contain from 1 to 100 mg of trichokirin conjugate or trichosanthin conjugate.

What is claimed is:

1. An immunotoxin formed by the coupling of an antibody with trichokirin, having the following statistical formula:

P'—W—A' in which P' represents the radical of a protein P which is an antibody or antibody fragment, A' represents the radical of a protein A which is trichokirin, and W represents a divalent covalent structure containing at least one thioether group or one disulfide group in which one of the sulfur atoms is selected from the sulfurs of the cysteines of P or A or is bonded to the groups belonging to P and/or A by spacing structures carrying a functional group bonded to the said groups belonging to P and A.

2. An immunotoxin formed by the coupling of an antibody with trichokirin having the following statistical formula:

P'—W'—A' in which P' and A' are as defined in claim 1 and W' represents a covalent structure selected from the group consisting of:

(a) a group of the formula:

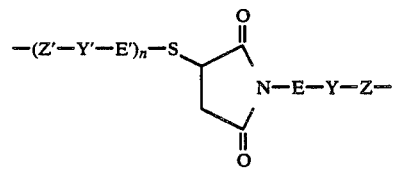

(b) a group of the formula:

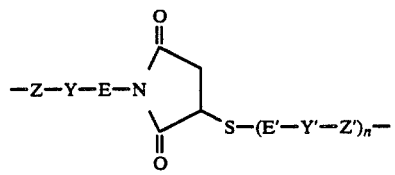

(c) a group of the formula:

—Z'—Y'—E'—S—S—(E—Y—Z)$_n$ and (d) a group of the formula:

—S—S—(E—Y—Z)$_n$ in which:

Z and Z', which are identical or different, represent the groups belonging to the proteins A and P, and are chosen from:

the oxygen atom originating from the hydroxyl of one of the tyrosine residues;

the carbonyl group originating from one of the terminal carboxyls or the free carboxyls of the aspartic and/or glutamic acids of A and P;

the group originating from the dialdehyde structure obtained after oxidation of the carbohydrate structure of P or of the protein A with periodic acid; or the —NH— group originating from one of the terminal amines of A and P or from one of the amines in the epsilon position of one of the lysine residues;

Y and Y' represent any group which is capable of being covalently bonded to any one of the groups Z and Z' of the proteins A and P;

E and E' represent divalent organic radicals; and n represents zero or 1.

3. An immunotoxin having the following statistical formula:

P'(W'—A')$_m$ in which W' is as defined in claim 2, m varies from 0.3 to 12, P' represents the radical, of a protein P which is an antibody or antibody fragment, and A' represents the radical of a protein.

4. An immunotoxin according to claim 1, wherein the protein A is the modified trichokirin represented by the formula:

$$TK^*—(CO—\underset{\underset{CH_2COOH}{|}}{CH}—S—Q)_p$$

in which TK$^b$ represents the trichokirin radical, Q represents hydrogen or the acetyl group and P can vary between 0.2 and 3.

5. An immunotoxin as claimed in claim 3, having the following statistical formula :

$$P'+NH—CO—CH_2CH_2—S—S—\underset{\underset{CH_2COOH}{|}}{CH}—CO—NH—TK')_m$$

in which P' and m are as defined in claim 3 and TK' is the radical or trichokirin, from which amino functions have been removed.

6. An immunotoxin as claimed in claim 3, having the following statistical formula:

P'—(NH—CO—CH₂CH₂—S—S—CH₂C-H₂—CO—O—TK")ₘ in which P' and m are as defined in claim 3 and TK" is the radical or trichokirin, from which phenolic hydroxyl groups have been removed.

7. Pharmaceutical compositions containing an immunotoxin as claimed in claim 1 as the active principle with a pharmaceutically acceptable carrier.

8. A process for the preparation of an immunotoxin having the following statistical formula:

P'—W—A' in which P' represents the radical of a protein which is an antibody or antibody fragment, A' represents the radical of a protein A which is trichokirin, and W represents a divalent covalent structure containing at least one thioether group or one disulfide group in which one of the sulfur atoms is selected from the sulfurs of the cysteines of P or A or is bonded to the groups belonging to P and/or A by spacing structures carrying a functional group bonded to the said groups belonging to P and/or A, wherein a protein P₁, which is modified trichokirin or an antibody or antibody fragment, carrying at least one free thiol group attached to the said protein P₁ directly or via a spacing structure, is reacted, in aqueous solution and at room temperature, with a protein P₂ which is different from ₁, which is modified trichokirin or an antibody or antibody fragment, carrying a group capable of coupling with the free thiol of the protein P₁ to form a thioether or disulfide bond.

9. A process according to claim 8, wherein the protein derivative having the hereinbelow statistical formula is used as protein P₁ or P₂:

P₂"—O—CO—E—G (VI)

in which:
P₂" represents the radical of a protein selected from the group comprising:
any antibody or antibody fragment, any immunoglobulin or immunoglobulin fragment or any molecule derived from these molecules by modification of any one of their functional groups; and
trichokirin or any molecule derived from the said toxins by modification of any one of their functional groups, the said radical being the protein from which one or more phenolic hydroxyl groups of the tyrosines have been removed;

the oxygen atom is that belonging to the phenolic hydroxyl groups missing from the radical P₂"; and
E is as defined in claim 3, and
G represents a group:

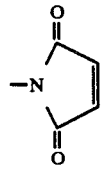

or a group —S—S—X wherein X is an activating group.

10. A process according to claim 8, wherein the protein A is the modified trichokirine of formula:

TK*—(CO—CH—S—Q)ₚ
         |
         CH₂COOH in which TK* represents the trichokirin radical, Q represents hydrogen or the acetyl group and p can vary between 0.2 and 3.

11. A process according to claim 8, for the preparation of an immunotoxin having the statistical formula:

P'—(NH—CO—CH₂—CH₂—S—S—CH—CO—NH—TK')ₘ (IIIa)
                              |
                              CH₂—COOH wherein:
P' and m are as defined in claim 4 and TK' is the radical of trichokirine, from which amino functions have been removed which consists in reacting, in an aqueous solution and at the ambient temperature, a protein P₁ which is an antibody or an antibody fragment bearing at least one free thiol group attached to the said protein P₁ directly or via a spacing structure, with the mercaptosuccinoyl-trichokirine as protein P₂.

12. A process according to claim 8 for the preparation of an immunotoxin having the statistical formula:

P'—(NH—CO—CH₂—CH₂—S—S—CH₂—CH₂—CO—O—TK")ₘ in which P' and m is as defined in claim 4 and TK" is the radical of trichokirin, from which phenolic hydroxyl groups have been removed which consists in reacting, in an aqeous solution and at the ambient temperature a protein P₁ which is an antibody or an antibody fragment bearing at least one free tiol group attached to the said protein P₁ directly or via a spacing structure, with the 3-(2-pyridyl-disulfanyl)propionate of trichokirine.

* * * * *